US008062216B2

United States Patent
Raghuprasad

(10) Patent No.: US 8,062,216 B2
(45) Date of Patent: Nov. 22, 2011

(54) OTOSCOPE WITH ATTACHABLE EAR WAX REMOVAL DEVICE

(76) Inventor: Puthalath Koroth Raghuprasad, Odessa, TX (US)

( * ) Notice: Subject to any disclaimer, the term of this patent is extended or adjusted under 35 U.S.C. 154(b) by 254 days.

(21) Appl. No.: 12/502,367

(22) Filed: Jul. 14, 2009

(65) Prior Publication Data

US 2011/0015489 A1    Jan. 20, 2011

(51) Int. Cl.
*A61B 1/227* (2006.01)
(52) U.S. Cl. .......................... 600/200; 604/27; 604/257
(58) Field of Classification Search .................. 600/185, 600/187, 188, 199, 200, 205; 604/27, 150, 604/257, 43, 514
See application file for complete search history.

(56) References Cited

U.S. PATENT DOCUMENTS

| 3,398,743 | A | | 8/1968 | Shimon |
| 3,934,578 | A | | 1/1976 | Heine |
| 4,785,796 | A | | 11/1988 | Mattson |
| 5,107,861 | A | | 4/1992 | Narboni |
| 5,309,899 | A | | 5/1994 | Ginsberg |
| 5,527,275 | A | | 6/1996 | Ginsberg |
| 5,685,851 | A | | 11/1997 | Murphy et al. |
| 5,916,150 | A | * | 6/1999 | Sillman .......................... 600/184 |
| 5,961,441 | A | | 10/1999 | Plumb et al. |
| 6,001,059 | A | | 12/1999 | Elliott |
| 6,106,457 | A | * | 8/2000 | Perkins et al. ................. 600/175 |
| 6,152,873 | A | * | 11/2000 | Rogers .......................... 600/200 |
| 6,210,358 | B1 | * | 4/2001 | Roger ............................ 604/43 |
| 6,416,464 | B2 | | 7/2002 | Elliott |
| 6,949,088 | B2 | | 9/2005 | Macrae |
| 7,988,657 | B2 | * | 8/2011 | Shapiro et al. .................. 604/27 |
| 2005/0004519 | A1 | | 1/2005 | Van Jaarsveldt |
| 2005/0143626 | A1 | | 6/2005 | Prescott |
| 2006/0182296 | A1 | | 8/2006 | Bauman |
| 2007/0009368 | A1 | | 1/2007 | Yang |
| 2007/0106204 | A1 | * | 5/2007 | Fedenia et al. ................. 604/28 |
| 2007/0156173 | A1 | | 7/2007 | Carnahan |
| 2007/0167918 | A1 | * | 7/2007 | Reed et al. ..................... 604/187 |
| 2008/0139888 | A1 | * | 6/2008 | Strom et al. ................... 600/200 |
| 2008/0183125 | A1 | | 7/2008 | Issa |
| 2009/0048579 | A1 | * | 2/2009 | Glassman et al. ............. 604/514 |

FOREIGN PATENT DOCUMENTS

| EP | 0243261 | 10/1987 |
| EP | 1941921 | 7/2008 |
| JP | 2004267224 | 9/2004 |
| WO | 0121118 | 3/2001 |
| WO | 2007035079 | 3/2007 |

* cited by examiner

*Primary Examiner* — Eduardo C Robert
*Assistant Examiner* — Atiya Mahmud
(74) *Attorney, Agent, or Firm* — David L King

(57) ABSTRACT

An otoscope kit has an otoscope with an attachable ear wax removal device for ear wax removal. A fluid dispensing means which is attachable to the otoscope for ejecting fluid through said ear speculum into the ear canal, the fluid dispensing means being mounted on the gripping body of the otoscope. The fluid dispensing means preferably includes a housing, a fluid supply and dispensing container, a pump, a tube connected to the fluid supply and dispensing container at one end extending and connected to a connector on a speculum cover. The fluid dispensing means is controlled by an actuator switch that is mounted in an opening of said housing wherein the actuation of the fluid dispensing means occurs without blocking the line of sight through the viewing means. The fluid dispensing means further can have a fluid recovery means having a vacuum pump, a fluid and debris recovery container and a tube for connecting the fluid recovery container to a second connector in the speculum cover. The fluid recovery means is controlled by a second actuator switch mounted in an opening of the dispensing housing. The otoscope-come ear wax removal system has the main advantage of removing ear wax under direct vision.

17 Claims, 12 Drawing Sheets

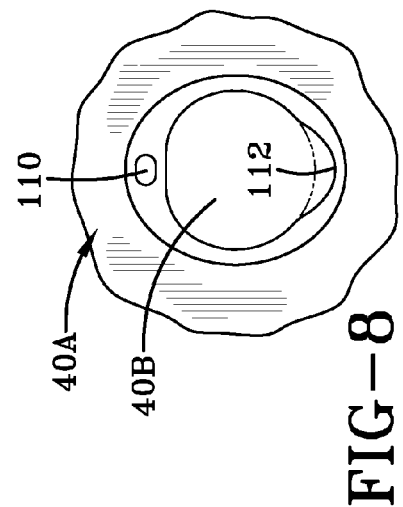
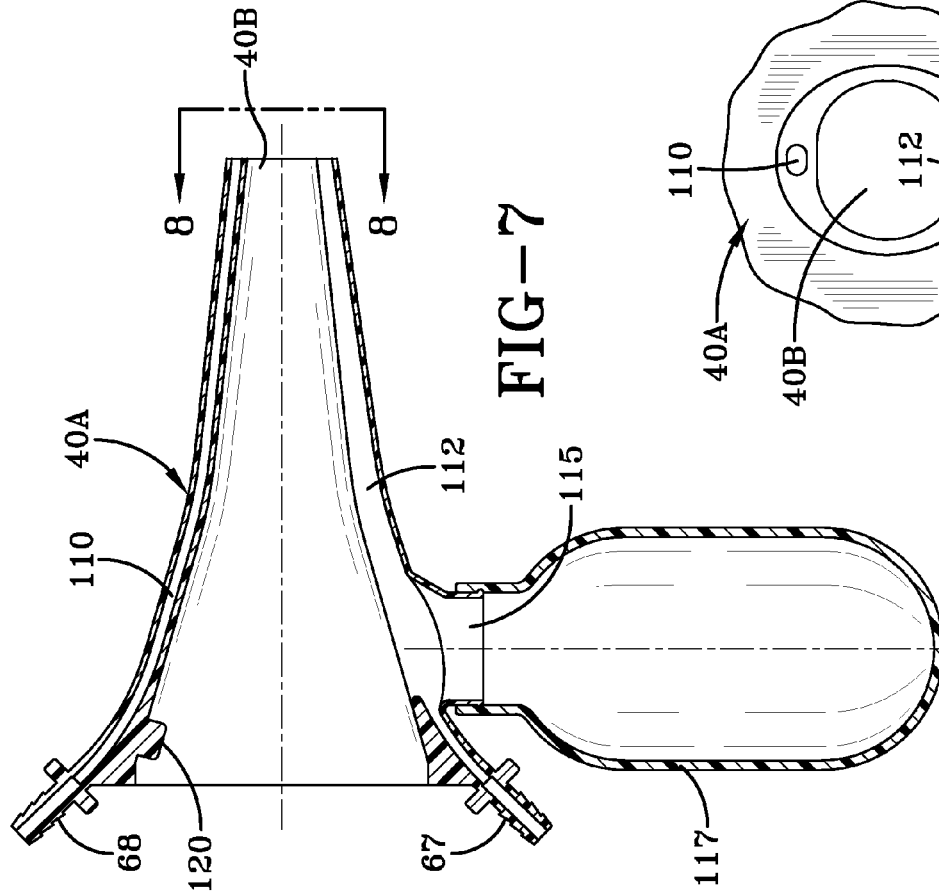
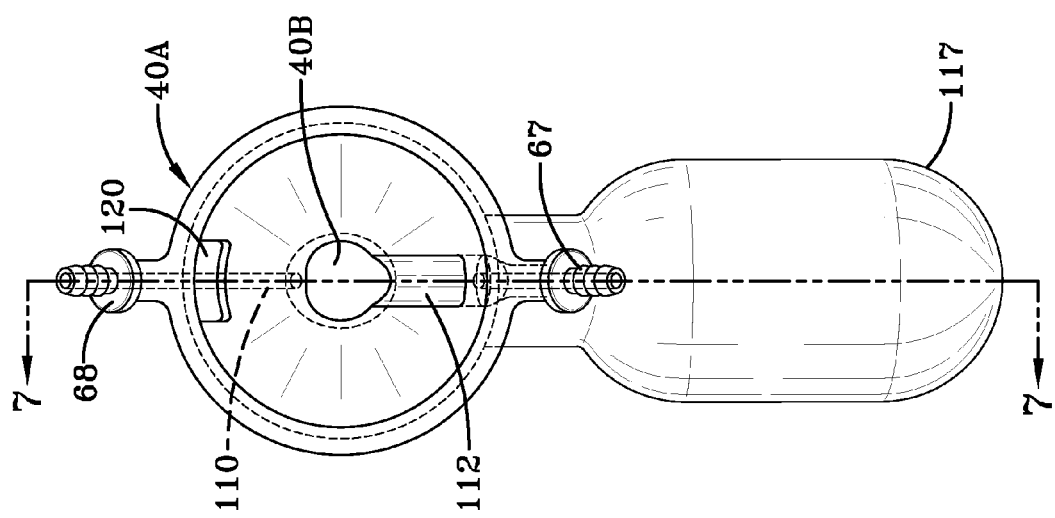

OTOSCOPE WITH ATTACHABLE EAR WAX REMOVAL DEVICE

TECHNICAL FIELD

The present invention relates to a device for removing ear wax or cerumen from the ear canal while providing a means for viewing the ear canal during the wax removal.

BACKGROUND OF THE INVENTION

Cerumen or ear wax is a waxy substance produced in the ear canal. Wax buildup is due to accumulation of cerumen as well as dirt and debris. However, excess production or impaction of cerumen can press painfully against the ear drum and can also impair hearing. Ear wax buildup can also interfere with hearing aids.

There are several methods of removing excess cerumen. A common method is to syringe the ear canal with warm water flushing the cerumen out with the water. Various solutions of oils, peroxide, glycerine or detergents are also used to flush the ear canal. Cotton swabs are also commonly used, but not recommended as they generally only remove a small amount of wax and push the rest further into the ear canal.

Physically picking or scraping the earwax out with an ear pick or curette is yet another method of removing ear wax usually performed by a health professional under direct observation with magnification.

A less common method is ear candling which is the practice of lighting a specially made hollow ear candle and placing the unlit end in the patient's ear. It is claimed to create a slight vacuum that draws out debris and wax.

There are some complications or risks associated with these various types of ear wax removal such as damage to the ear drum from excess pressure or physically perforating the ear drum.

A key limitation in the removal of ear wax or cerumen is the inability to directly observe the ear canal. A device called an otoscope provides a way to see into the ear canal. The otoscope has a handle and a head with a light source and a magnifying lens with a removable ear speculum that attaches to the front. The speculum is inserted into the external ear canal allowing the examiner to look through the lens into the ear canal. Many models have a detachable sliding rear window allowing instruments to be inserted through the speculum into the ear canal that could be used for removing ear wax. The otoscope can only be used to observe the ear canal before or after flushing, but not during actual ear wax removal as a result the physician must repeatedly stop flushing to observe the progress being made.

An object of the present invention is to be able to visually observe the ear wax removal during flushing or vacuuming of the fluid and dislodged debris from the ear canal. This objective is achieved as are other features by the use of the present invention described as follows.

SUMMARY OF THE INVENTION

An otoscope kit has an otoscope and an attachable ear wax removal device for ear wax removal. The otoscope has an elongated gripping body; a hollow conical ear speculum, having a small outer end with a protective soft collar adapted to be placed in the entrance of the ear canal of a patient, the ear speculum being transversely connected to a top end of the gripping body; a viewing means connected to said top end of the gripping body to provide a line of sight through said ear speculum; a light source which is directed through the ear speculum; and a fluid dispensing means which is removably attached to the otoscope for ejecting fluid through an ear speculum cover into the ear canal, the fluid dispensing means being secured to the gripping body of the otoscope. The attachable ear wax removal device is a fluid dispensing means which preferably includes a dispensing housing, a fluid supply and dispensing container, a pump, a tube connected to the fluid supply and dispensing container at one end extending and connected to an opening in the speculum cover. The fluid dispensing means is controlled by an actuator switch that is mounted in an opening of the dispensing housing wherein the actuation of the fluid dispensing means occurs without blocking the line of sight through the viewing means.

The speculum is removably attached to the top end of the gripping body. The speculum cover is adapted to fit onto the speculum without blocking the covering opening. The speculum cover has a fluid delivery passageway with a connector for sealingly engaging the tubing to form a fluid path from the fluid supply and dispensing container through the speculum cover for delivering fluid into the ear canal. The speculum cover fluid passageway has an inlet connector end open through the passageway to an outlet end to make a fluid path through the speculum cover.

The fluid dispensing means further can have a fluid recovery means having a vacuum pump, a fluid and debris recovery container and a tube for connecting the fluid recovery container to a second connector in the speculum cover. The fluid recovery means is controlled by a second actuator switch mounted in an opening of the dispensing housing. The speculum cover has a second vacuum fluid passageway open to a second suction opening in the speculum cover and extending through the speculum cover to the second vacuum connector for attachment of a vacuum tube which is connected to the fluid and debris recovery container to form a fluid and debris recovery passageway for recovering fluid and debris from the ear canal into the fluid recovery container. The second vacuum passageway preferably is formed as a large channel open to the ear canal of the patient and extending back to a bowl shaped trap portion to which an ear wax debris container is connected to the speculum cover on a lower side of the speculum cover. In this way ear wax is drawn into the container under vacuum and falls into the debris container as the fluid is sucked out of the ear canal into the second vacuum passageway and tubing back into the fluid recovery container. The speculum cover when attached to the speculum seals the second vacuum passageway channel internally near the debris container.

Preferably, the fluid delivery passageway is positioned on an external surface of the speculum cover and the fluid and debris recovery passageway is positioned on a lower internal surface of the speculum cover. The otoscope has a power source for operating the otoscope. The power source can be an electrical cord connected to the gripping body for connecting a plug into an electrical outlet. Alternatively, the power source can be one or more batteries stored in the gripping body and fluid dispensing means and the otoscope can also include a recharging base for recharging the batteries. The speculum cover can be disposable for replacement after each use as can be the fluid supply and dispensing container and the fluid recovery container and tubing or alternatively can be reused after cleaning and disinfecting.

BRIEF DESCRIPTION OF THE DRAWINGS

The invention will be described by way of example and with reference to the accompanying drawings in which:

FIG. 6 is a cross sectional view of the tube attachment to the speculum cover for the fluid dispensing means of the present invention.

FIG. 7 is a longitudinal cross sectional view of the speculum cover and tube attachment for the fluid dispensing means of the present invention.

FIG. 8 is a plan view of the end of the speculum cover with fluid passageway and secondary vacuum passageway openings according to the present invention.

DETAILED DESCRIPTION OF THE INVENTION

Figure 1:
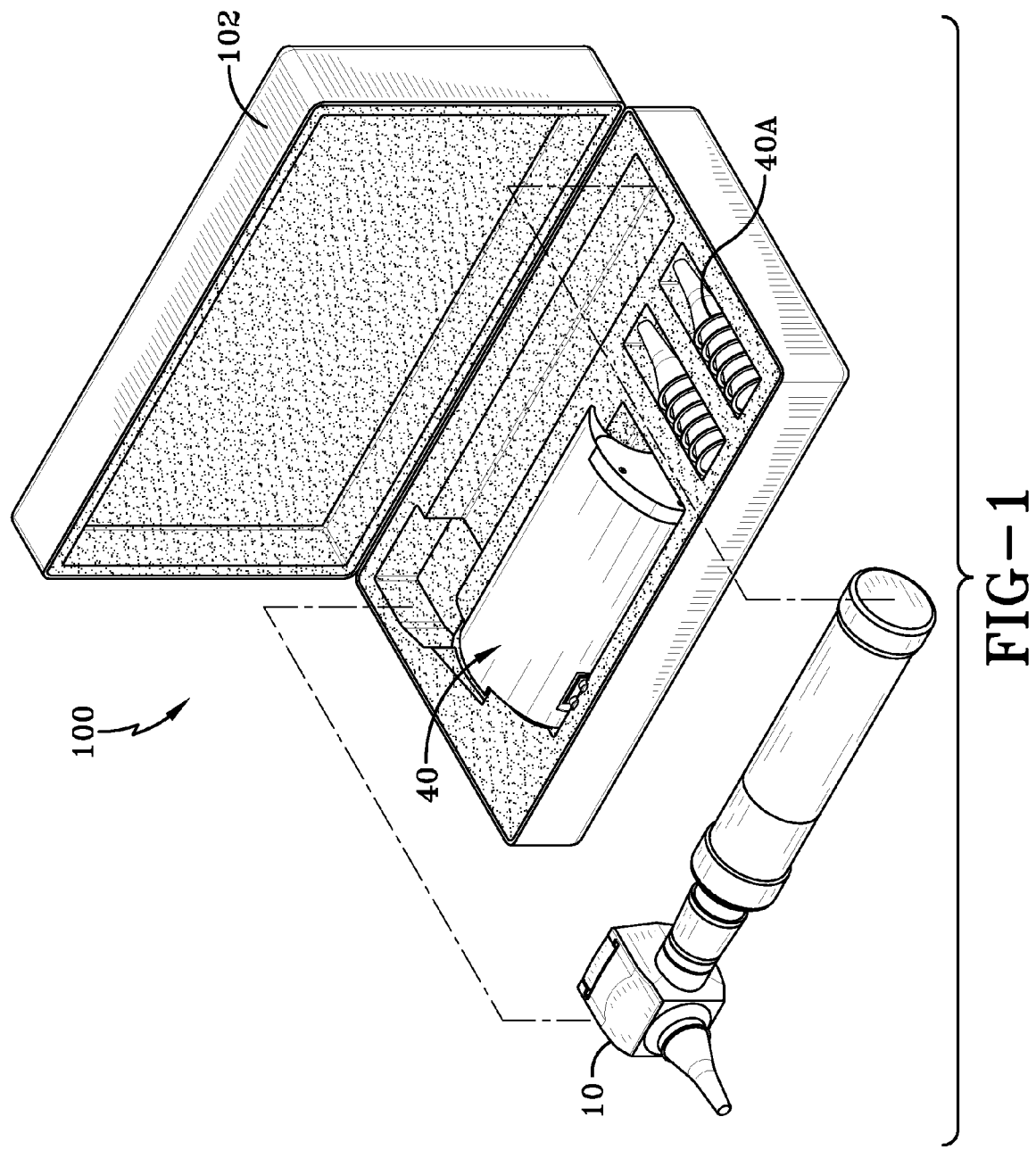
FIG. 1 is a perspective view of the otoscope kit of the present invention.

With reference to FIG. 1, an otoscope kit 100 of the present invention is shown. The otoscope kit 100 includes an attachable ear wax removal device hereinafter referred to as a fluid dispensing means 40 that can be physically attached to an otoscope 10. In addition, the kit 100 includes several removable ear speculum covers 40A all contained in a box 102.

Figure 2:
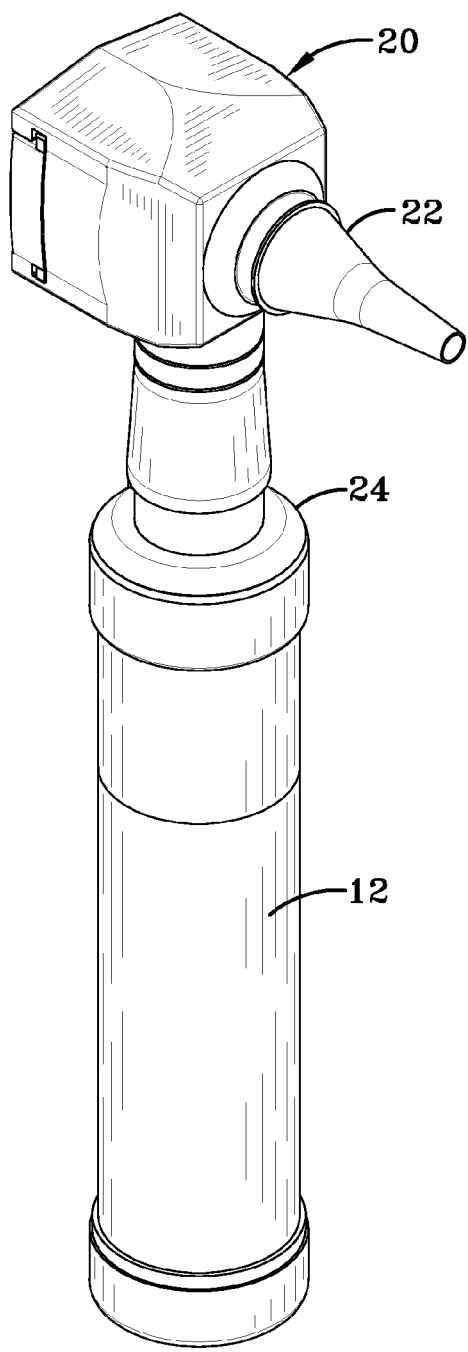
FIG. 2 is a perspective front view of the otoscope of the present invention.
Figure 3:
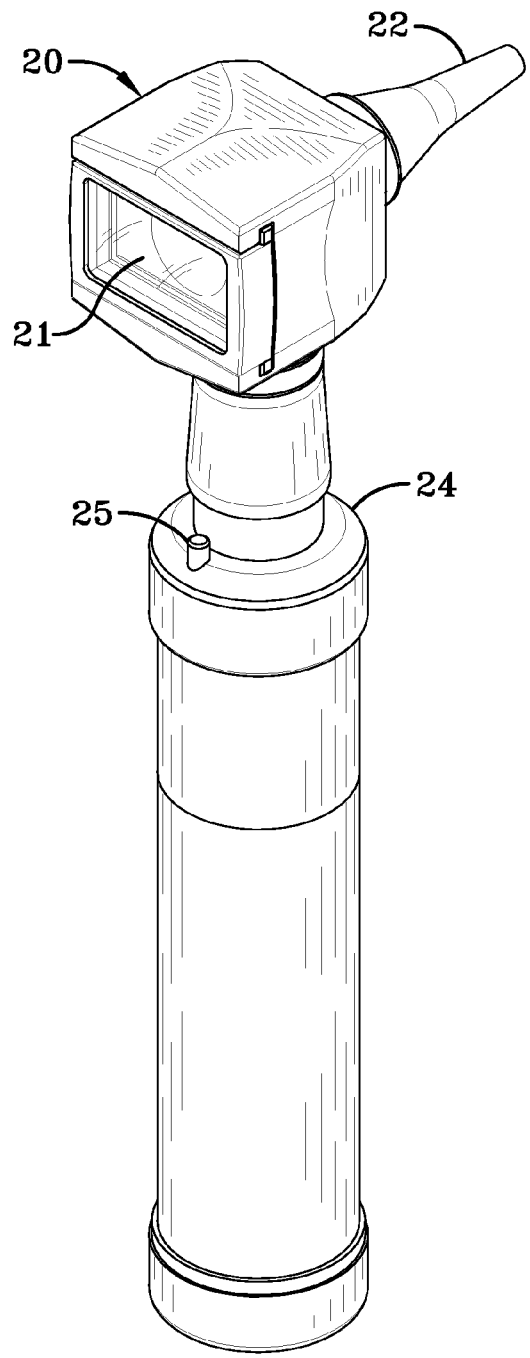
FIG. 3 is a perspective rear view of the otoscope of the present invention.
Figure 13:
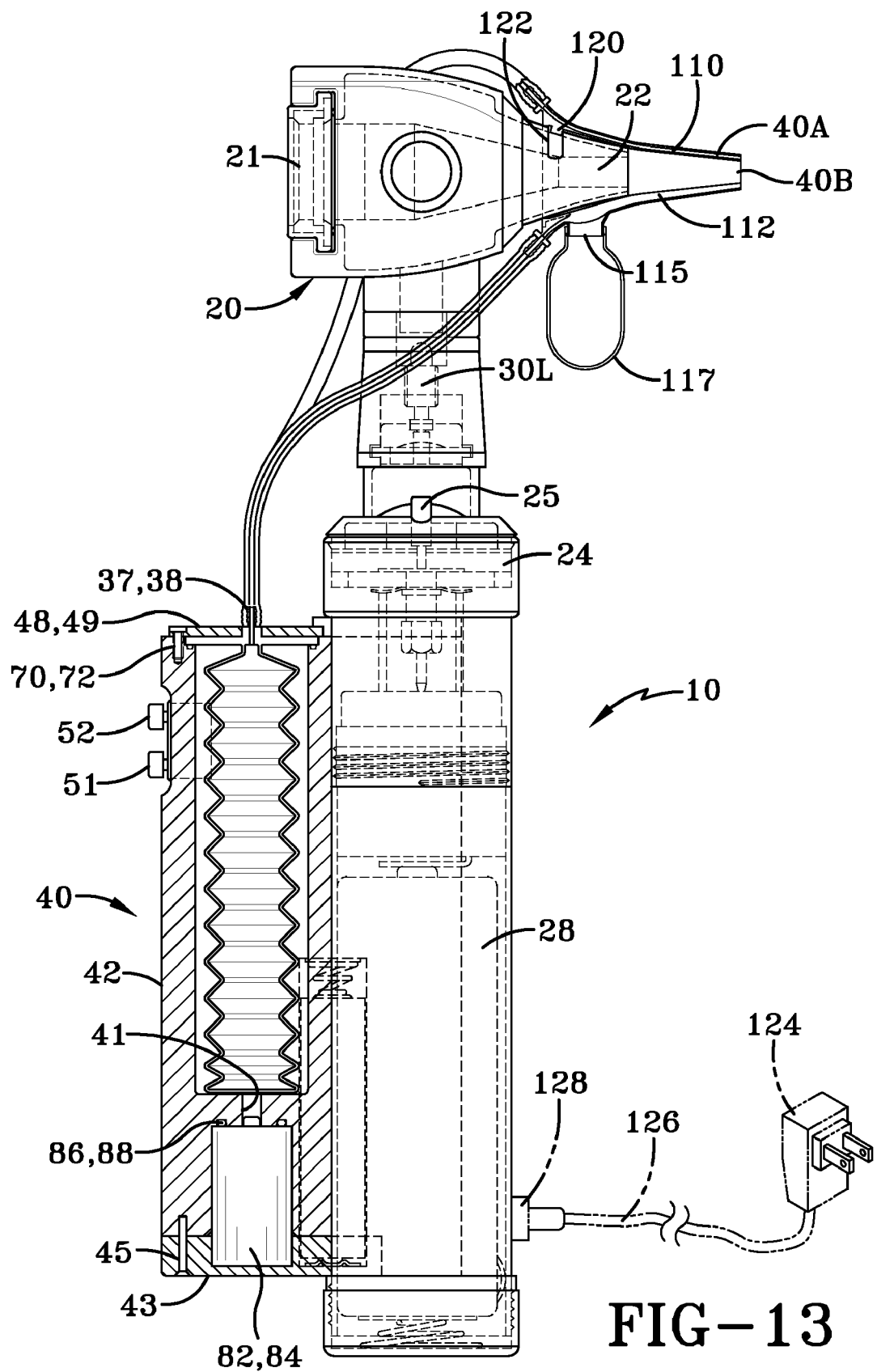
FIG. 13 is a cross sectional view of the otoscope with attached fluid dispensing means according to the present invention.

As further illustrated in FIGS. 2 and 3, the otoscope has an elongated gripping body 12 and a hollow conical ear speculum 22 having a small outer end adapted to be placed in the ear canal of the patient. The ear speculum 22 is transversely connected to a top end 20 rotatably attached to the otoscope gripping body 12. A viewing means or window 21 is connected to the top end 20 of the otoscope 10 to provide a line of sight through the ear speculum 22 directly into an ear canal. As further shown in FIG. 13, a light source 30L is provided internal of the otoscope 10 which directs light through the ear speculum 22. This light source 30L impinges upon a lens internal of an otoscope 10 such that the observer can see a view of the inner ear canal 4 through the viewing window 21. As shown, the viewing window or means 21 along with the top 20 can be pivotally rotated about the gripping body 12. On the upper surface of an end cap 24 of the otoscope 10 is provided a switch 25 upon which the light 30L can be energized from an internal battery 28 inside of the otoscope. This is illustrated in FIG. 13. The ability to rotate the viewing window or means 21 relative to the gripping body 12 enables the unit to be moved in any particular fashion. Also, the light intensity can be adjusted by rotation of this viewing window if so desired. The otoscope 10 can be powered by a battery 28, the battery preferably is rechargeable and can be connected to an outlet through the connector 128 and wires 126 and 124 as shown in phantom or dashed lines.

Figure 4:
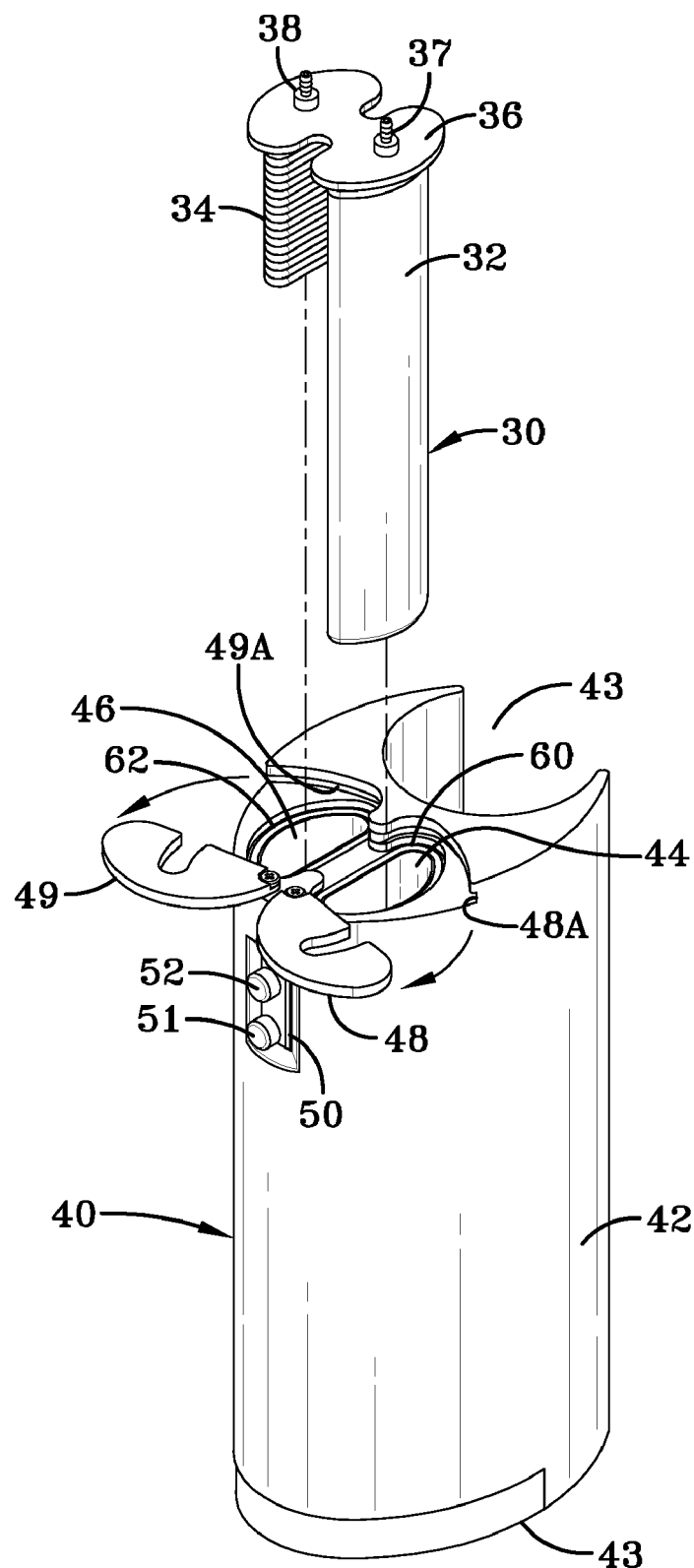
FIG. 4 is an exploded perspective view of the fluid dispensing means for attachment to the otoscope of the present invention.
Figure 5:
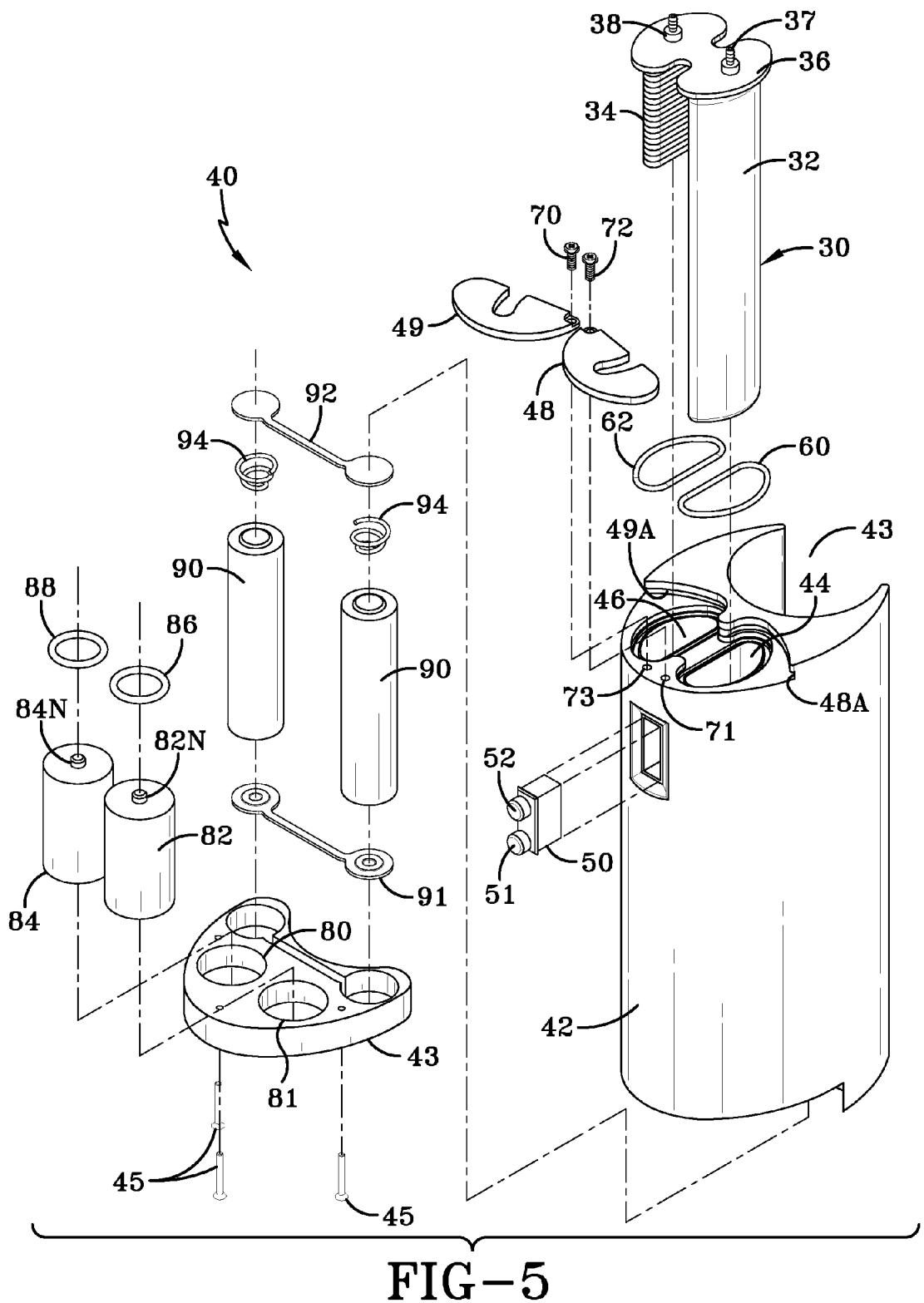
FIG. 5 is an exploded perspective view of the entire fluid dispensing means for attachment to the otoscope of the present invention.
Figure 12:
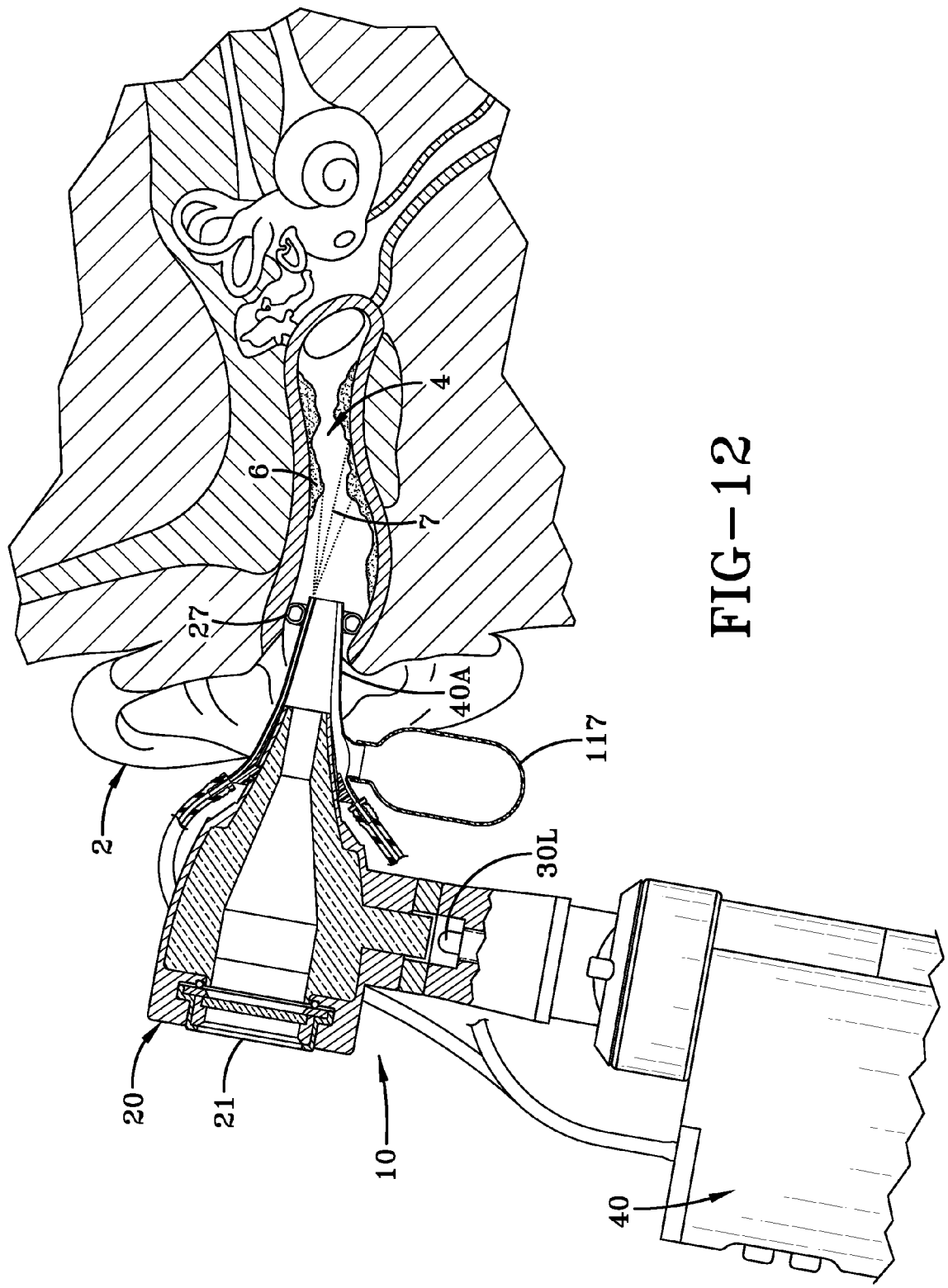
FIG. 12 is a cross sectional view of the otoscope with attached fluid dispensing means being used in a patient's ear canal.
Figure 12A:
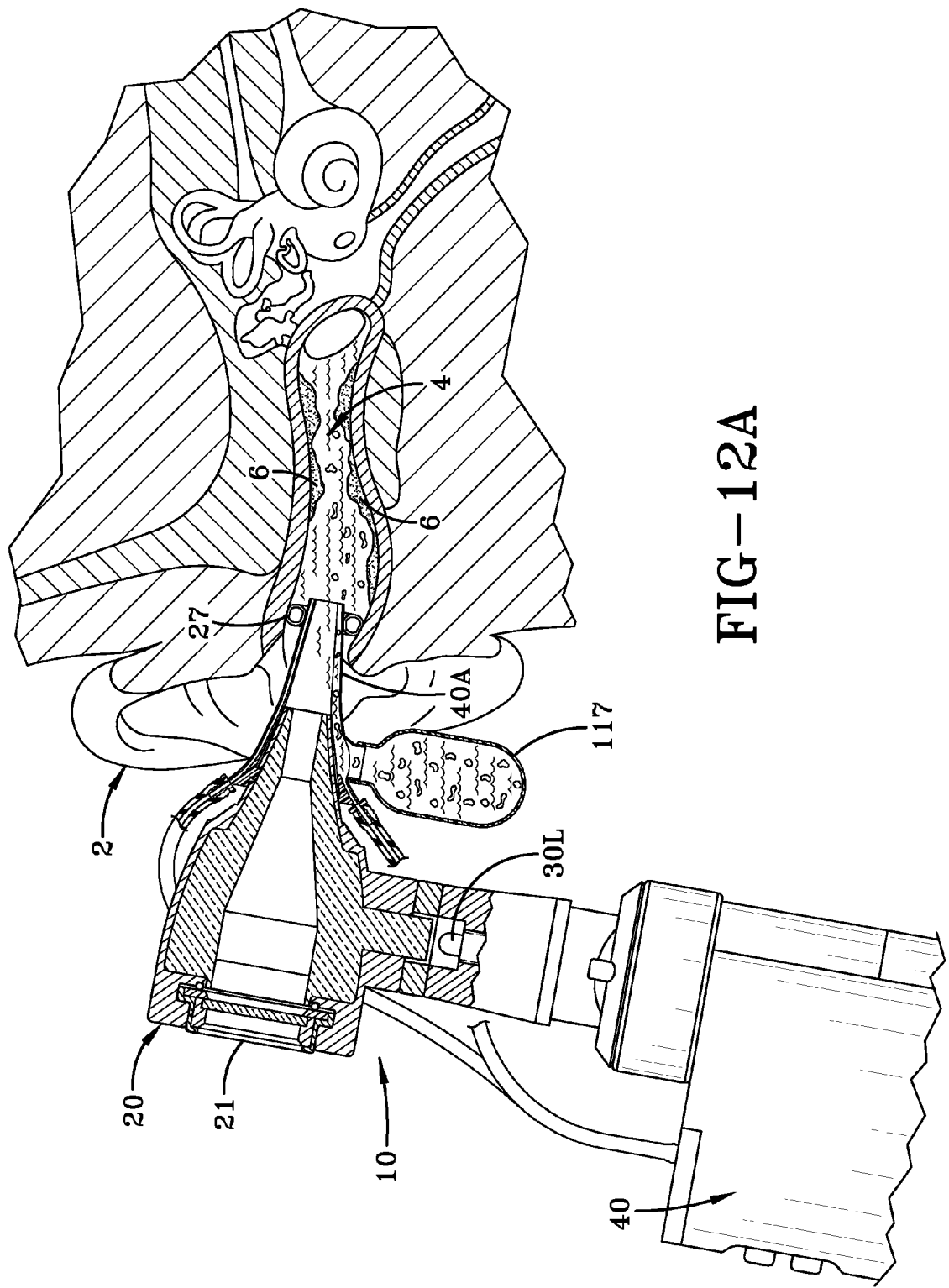
FIG. 12A shows the removal of ear wax through the vacuum recovery means.

The otoscope 10 as illustrated in FIGS. 2 and 5, provides a means for viewing the inner ear canal and enables the viewer to slide the viewing means or window 21 over slightly to insert tools or utensils into an opening and through the speculum 22 into the ear canal if so desired. These principles are typically known and this otoscope is conventionally considered somewhat standard relative to existing otoscopes. In addition to the otoscope 10, the kit 100 includes a unique fluid dispensing means 40 that can be removably attached to the gripping body 12 of the otoscope. Alternatively, this fluid dispensing means 40 can be sold separately and can be used with available otoscopes. This fluid dispensing means 40, illustrated in FIGS. 4, 5, 9 and 10 as well as FIG. 13, provides a unique system that enables the physician to look into an ear canal 4 of a patient 2 and to deliver fluid 7 and remove fluid 7 and ear wax 6 from the ear canal 4 in an attempt to remove cerumen or ear wax 6 from the patients inner ear as shown in FIGS. 12 and 12A. As shown in FIG. 4, the fluid dispensing means 40 includes a housing 42, with a semicircular recess 43 extending longitudinally along the housing in such a fashion that it is possible to snap the entire fluid dispensing means 40 onto the otoscope gripping body 12. The housing 42 further includes two large cavities 44, 46 into which a fluid supply and recovery assembly 30 can be inserted into the housing body cavities 44 and 46. As shown, the assembly 30 includes a fluid supply and dispensing container 32 and a compressed but expandable fluid recovery container 34 both of which are connected to a plastic end plate 36. The plastic end plate 36 includes tubing connections 37 and 38. The tubing connection 37 is connected to the fluid supply and dispensing container 32 and the fluid connector 38 is connected to fluid recovery container 34. The recovery container 34 fits into the opening 46 where the fluid container 32 inserts directly into the opening 44, once these are inserted into the openings 44 and 46, the cover plate 36 is pushed firmly into place and compresses elastomeric seals 60, 62 when end caps 48 and 49 are respectively rotated into the slots 48A and 49A respectively to a closed position creating a sealed closure of the device.

With reference to FIG. 5, these components are shown in an exploded view wherein the housing 42 further includes a switch mechanism 50 which includes a first button 51 and a second button 52. These buttons or switches enable either a fluid pump motor 82 to be activated or a vacuum pump motor 84 to be activated that will be discussed later. In addition, the assembly 30 prior to being inserted into the housing 42 has the outer plate 36 resting over two "o" rings 60 and 62 as illustrated. Therefore, once the assembly 30 is inserted into the housing the top plate 36 rests upon the seals 60 and 62. Threaded fasteners 70 and 72 are inserted into the threaded openings 71 and 73 respectively to secure the end closures 48 and 49. Once the assembly 30 is inserted into the housing 42, the end closures 48 and 49 are rotated into position into the slots 48A and 49A respectively which forces the plate 36 into an airtight seal against seals 60, 62 in the container housing 42. A bottom plate 43 is attached to the housing 42. The bottom plate 43 includes recesses 80 and 81 into which a fluid dispensing pump 82 and a vacuum pump 84 and can be inserted. Directly above the fluid pump 82 and the vacuum pump 84 are seal "o" rings 86 and 88. Upon assembly these pumps and seals will press against an internal portion of the housing 42 through a pair of holes 41 (FIG. 13) through which the pump ends 82N and 84N project into and are open to the openings 44 and 46 at the lower end of the housing 42 which is open to the fluid supply and dispensing container 32 and the vacuum recovery container 34 upon assembly as shown in FIG. 13. These pumps can, in the case of the fluid pump 82 deliver compressed air into the opening 44 thus collapsing the fluid filled container 32 as the fluid is pumped into the ear canal 4. The vacuum pump 84 sucks air through the other hole 41 out of the opening 46 causing the collapsed fluid recovery container 34 to expand by creating a vacuum to draw fluid and ear wax debris from the ear canal during the ear wax removal procedure.

To operate the pump and vacuum motors a pair of batteries 90 is provided. The batteries 90 are connected electrically by connectors 91 and 92 at both ends. A pair of coil springs 94 is provided to ensure adequate electrical connection forces. The fluid dispensing means 40 can be powered in such a fashion that the pumps 82, 84 can be activated independently by the switches 51 and 52. Alternatively, both switches 51 and 52 can be depressed and activate both the fluid pump 82 and vacuum pump 84 simultaneously, if so desired. The bottom plate 43 is physically attached to the housing using threaded fasteners 45 and has a fit that allows the air to vent out of the bottom plate 43 as a vacuum is produced in the fluid recovery opening 46.

Figure 9:
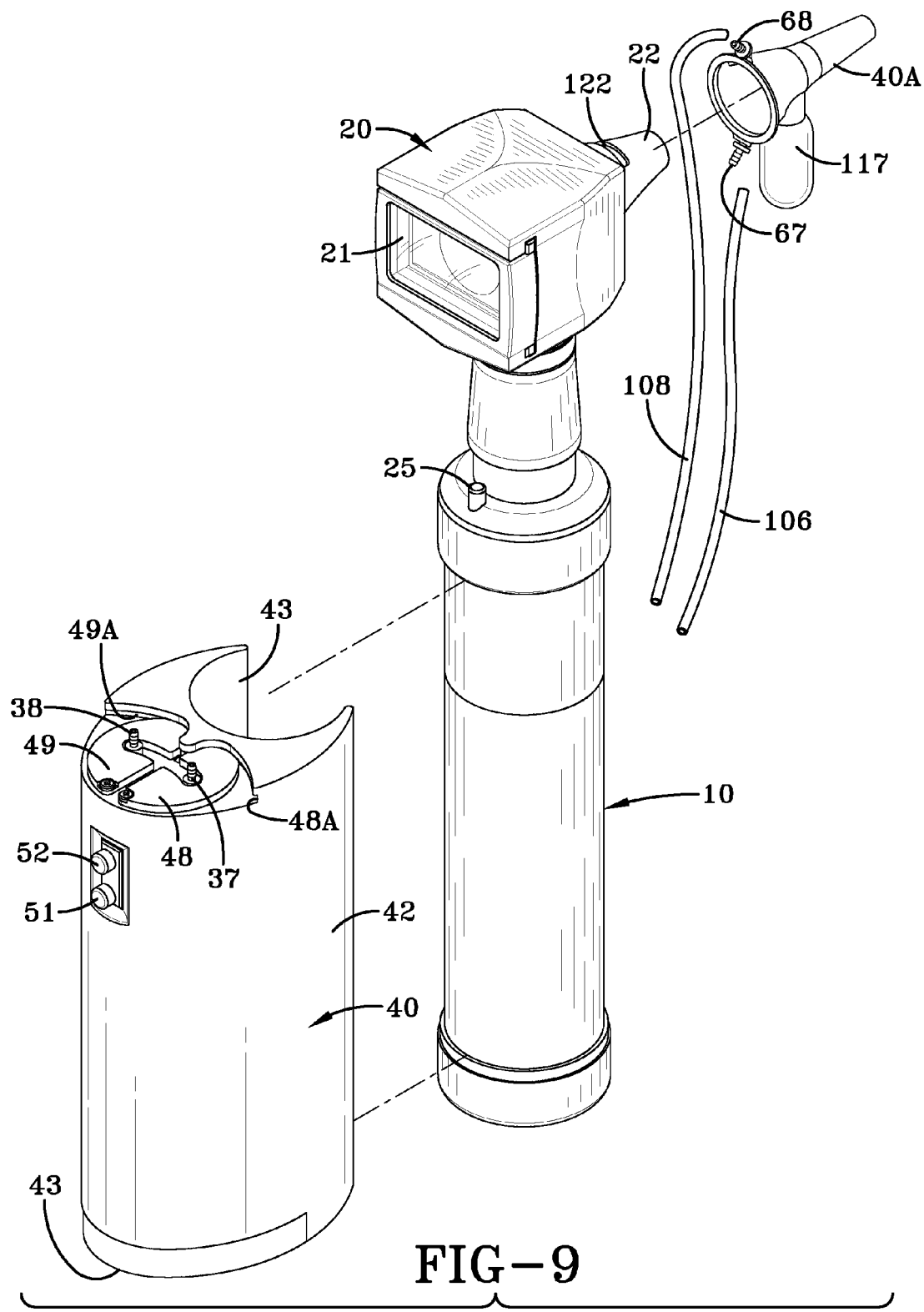
FIG. 9 is a perspective exploded view showing the recommended attachment of the fluid dispensing means prior to attachment to the otoscope according to the present invention.

With reference to FIG. 9, an exploded view of the otoscope 10 with the fluid dispensing means 40 not yet attached to the otoscope 10 is illustrated. The figure also shows a pair of tubes 106 and 108 extending on one side of the otoscope 10 toward an ear speculum cover 40A. The tubing 106 and 108 are adapted to connect to tubing connections 37 and 38 as illustrated and further to connect to the ear speculum cover 40A as further illustrated in FIGS. 6, 7 and 8.

With reference to FIG. 6, the ear speculum cover 40A has a pair of tubing connections 67 and 68 to which the tubing 106 and 108 can be attached. Extending from the tubing connections 67 and 68 are a pair of passages 110 and 112. The passages 110 and 112 extend from the connections 67 and 68 to the end of the speculum cover 40A as illustrated in FIG. 8. These openings or passages 110, 112 extend to and terminate at the smaller end of the speculum cover 40A to provide a clear passageway directly into and out of the ear canal. As further illustrated in FIG. 6, an upper portion of the ear speculum cover 40A is a protrusion 120. This protrusion 120 will fit into a slot 122 on the ear speculum 22 of the otoscope 10. In this fashion the ear speculum cover 40A can be snap fit onto the ear speculum 22 of the otoscope 10 and make a secure attachment as shown in FIG. 13. As shown in FIGS. 6, 7 and 8; the ear speculum cover 40A is open and hollow, forming a conical opening 40B to fit onto the ear speculum 22 of the otoscope 10, however slightly more elongated. This cover 40A can extend directly into an ear canal and be open such that the viewing source 21 is totally unobstructed by the cover 40A leaving an open viewing path through the opening 40B so that the doctor can see directly into the patient's ear canal.

An important aspect of the ear wax removal device is the shape of the passageways 110 and 112. The small circular opening of passageway 110 delivers a jet or stream of fluid into the ear which can be directed to dislodge ear wax from an upper side of the speculum cover 40A. The second vacuum passageway 112 is shaped as an open channel of much larger area to allow loosened ear wax to be sucked along the channel back to a trap or opening 115 for capturing ear wax 6 into a debris container 117 as the fluid is withdrawn as shown in FIG. 12A excess fluid is vacuumed into the passageway back to the debris and fluid recovery container 34. The passageway channel deepens and widens as it approaches the trap 115. The speculum of the otoscope closes the open top of the channel directly above the trap 115.

Figure 10:
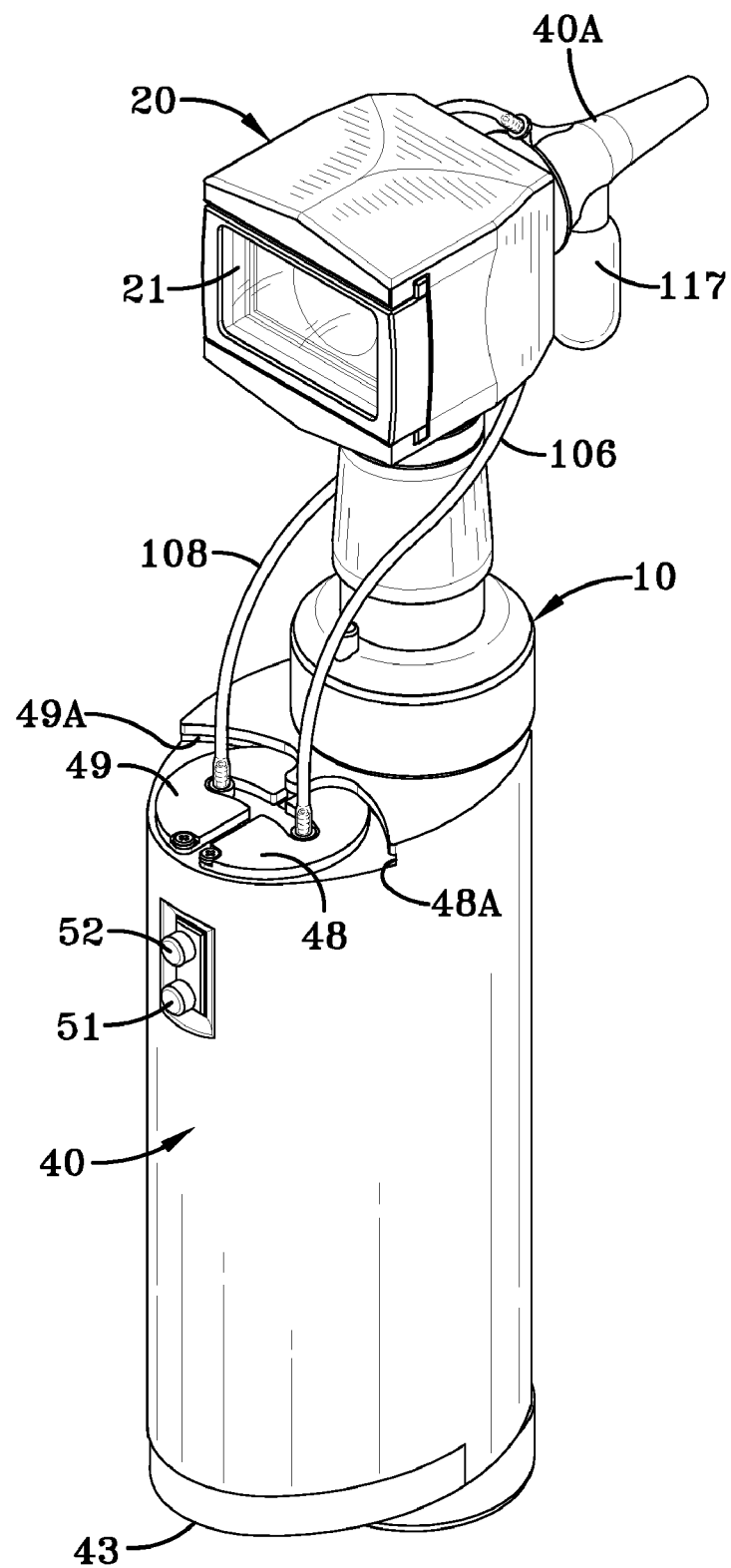
FIG. 10 is a perspective view showing the fluid dispensing means attached to the otoscope according to the present invention.

When completely assembled, the dispensing means 40 is snapped onto the gripping body 12 of the otoscope 10 as illustrated in FIG. 10. The tubing 106 and 108 are connected at both ends to tubing connections and directly attached to the removable ear speculum cover 40A. Once this assembly of the dispensing means 40 to the otoscope 10 is complete, as illustrated in FIG. 10, the patient's ear canal can be observed and ear wax or cerumen can be removed. In FIG. 12, the device according to the present invention is shown whereby the viewing source 21 of the otoscope 10 is shown wherein the lamp or light source 30L is illuminating into the inner ear canal 4 wherein the inner ear canal 4 is shown having fluid 7 sprayed under required pressure onto the wax 6, preferably the fluid 7 is a suitable warmed liquid and is delivered by pressing on the switch 52 which activates the pump 82 such that the fluid supply and dispensing container 32 is pressurized by air pressing against the flexible fluid supply and dispensing container 32 such that the fluid 7 is being pushed through the passageway 110 directly into the inner canal 4. An ear seal 27 is shown affixed at the small end or tip of the speculum cover 40A to create a seal in the ear canal 4 of the patient 2. As the ear wax 6 is softened or loosened either into small chunks of debris or preferably into a liquid form, a second switch 51 can be activated which will activate the vacuum pump 84 as shown in FIG. 12A. Upon activating the vacuum pump 84, the fluid 7 and wax debris 6 are drawn from the ear by the fluid vacuum pump 84 a debris container 117 and into the fluid recovery container 34 via the vacuum opening or passageway 112. Accordingly, as this wax debris 6 and fluid 7 are removed, additional fluid 7 can be added to the ear canal 4. All of this can be accomplished while viewing through the otoscope 10 in a normal fashion. This greatly facilitates the physician's ability to direct the fluid path most efficiently into the portions of the inner ear canal 4 where the most wax buildup is observed. Accordingly, this fluid dispensing means 40 enables the physician to directly remove the ear wax 6 while observing his activity of wax removal.

As illustrated, the fluid supply and dispensing container 32 preferably is a plastic flexible bag as is the vacuum fluid recovery container 34. These bags 32, 34 are provided in such a fashion that the activation of either the fluid pump 82 or the vacuum pump 84 can create a pressurization onto the container to press fluid out of the fluid supply and dispensing container 32 or create a vacuum on the vacuum fluid recovery container 34 of the fluid dispensing means 40 such that the bag 34 can be expanded internally to withdraw the excess fluid 7 from the ear canal 4 along with the ear wax 6 into the fluid recovery container 34. Once the wax removal procedure is completed, the entire fluid dispensing means 40 can be shut down, the ends 48 and 49 opened and the assembly 30 having both the fluid supply and dispensing container 32 basically depleted and the vacuum fluid recovery container 34 basically filled with the debris and fluid removed and then discarded, along with the tubing 108 and 106 and the ear speculum cover 40A. In this way, all bodily contaminated fluids coming from the ear canal can be safely discarded in biologically safe techniques known in art. This creates a hygienically clean assembly such that the fluid dispensing means 40 can remove all contaminated components which can simply be discarded and replaced with new components for use on the next patient.

Figure 14A:
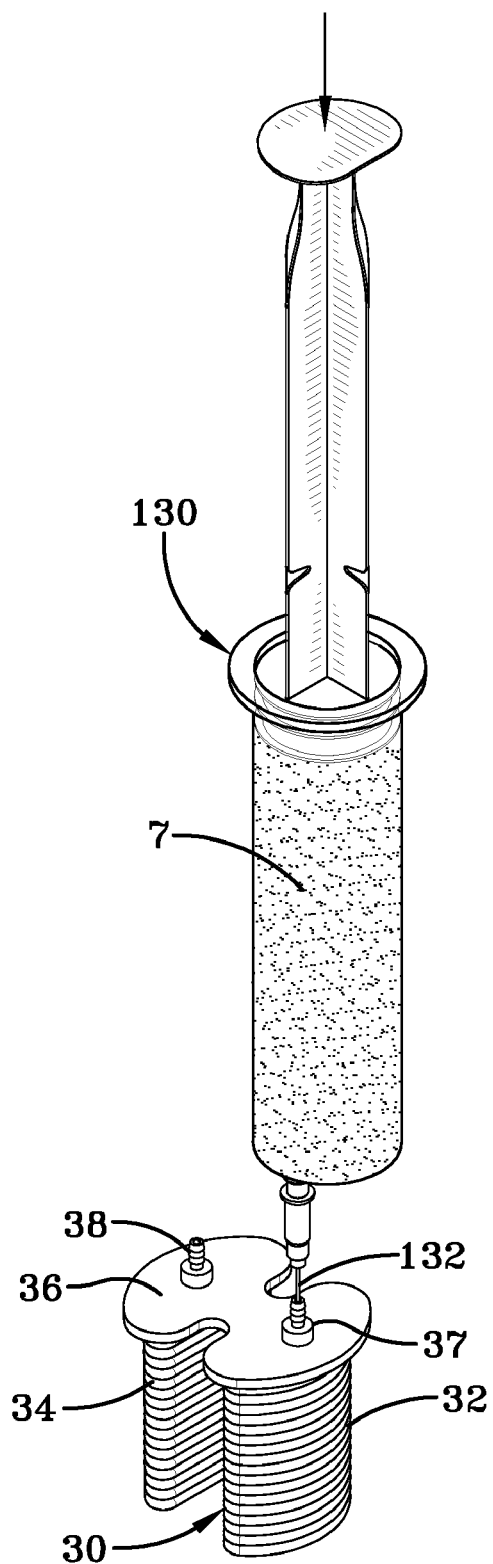
FIGS. 14A and 14B, 14A shows the fluid supply and recovery assembly prior to being filled, 14B shows the fluid supply and dispensing container being filled.
Figure 14B:
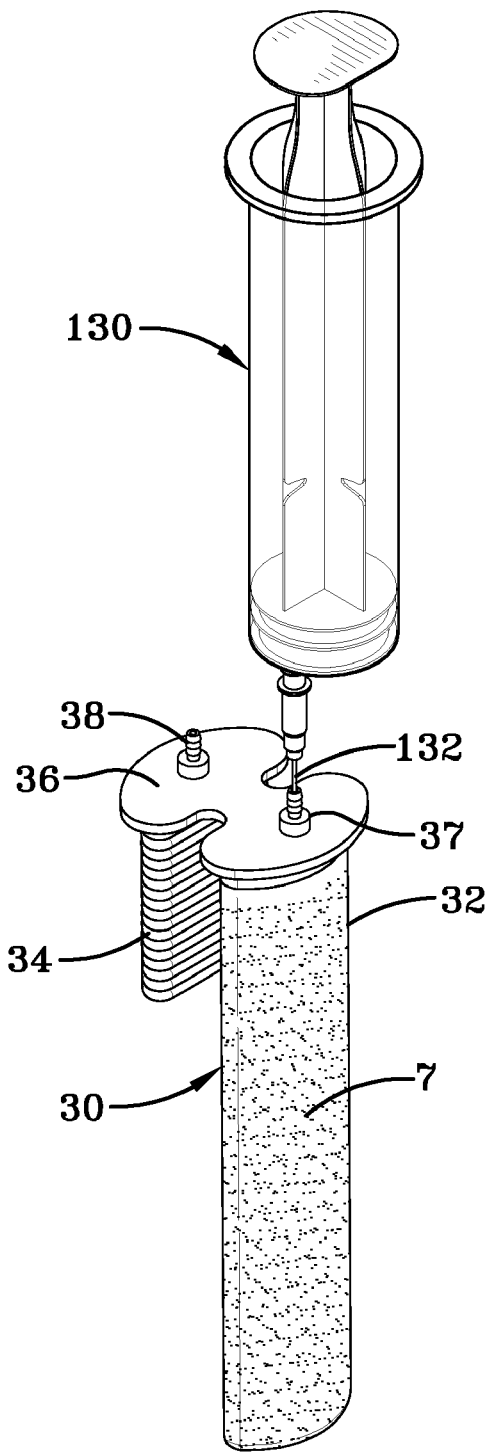

In FIGS. 14A and 14B, the fluid supply and recovery assembly 30 is shown. The supply and dispensing container 32 as well as the recovery container 34 are empty and the assembly 30 can be supplied as a replaceable component. As shown in FIG. 14B, the supply and dispensing container 32 can be filled in the doctor's office using an ear wax removal device such as a syringe 130 with a needle 132 connected to the fitting 37. The ear wax removal device preferably is filled with a suitable warmed solution 7. As shown, the container 32 holds approximately 57 cc of fluid. The recovery container 34 remains unfilled and has a similar fluid holding capacity of 57 cc. Once filled, the assembly 30 is inserted into the dispensing means 40 for use. Once used, the assembly 30 and the speculum cover 40A and tubing 106, 108 can be discarded.

Figure 11:
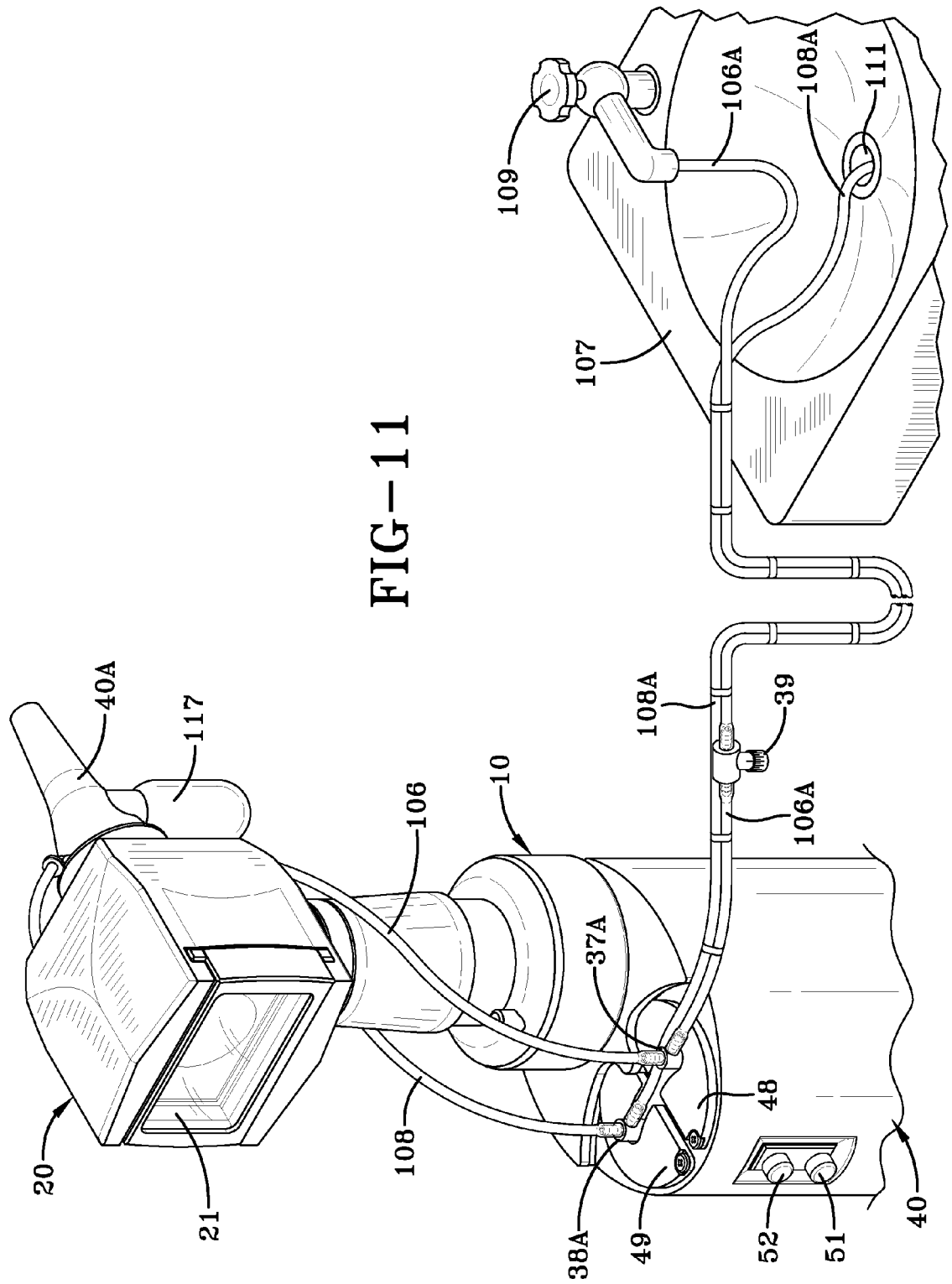
FIG. 11 is a perspective view of an alternative embodiment of the present invention showing a direct attachment to a faucet and drainage into sink.

In FIG. 11 an alternative embodiment of the present invention is shown wherein the fluid dispensing device 40 has been modified with connectors 37A and 38A that enable fluid supply tubing 106A to be connected to a water supply faucet 109 in a sink 107 forming a way to supply water directly to the fluid dispensing device 40. This provides the doctor with a virtually endless supply of warm or cold water. To recover this water, the fluid recovery side of the device 40 has drainage tubing 108A connected to the fitting 38A which has an end placed in the drain 111 of the sink 107. This enables the device to operate just as described previously but with the advantage of much increased fluid available for the procedure. As shown, the fluid supply connected to the faucet has a valve 39 which enables the flow to be regulated or turned on and off as desired.

As a further alternative, the tubing 106A and 108A can be directly attached to the fittings 67 and 68 of the speculum cover 40A and the entire device 40 can be eliminated if so desired. The advantage of this embodiment is greatly reduced cost. The main disadvantage is the lack of pump-driven fluid delivery actuated by a switch and the lack of vacuum power as the only vacuum created is a siphoning effect through the tubing 106A.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

I claim:

1. An otoscope kit with an attachable ear wax removal device for ear wax removal comprising:

an otoscope having an elongated gripping body; a hollow conical ear speculum, having a small outer end adapted to be placed in the ear canal of a patient, said ear speculum being transversely connected to a top end of the gripping body; a viewing means connected to said top end of the gripping body to provide a line of sight through said ear speculum; a light source which is directed through the ear speculum; and a fluid dispensing means which is removably attached to the otoscope for ejecting fluid through a speculum cover into the ear canal, the fluid dispensing means having a fluid dispenser housing for holding a fluid supply container and dispenser, the fluid dispenser housing being mounted on the gripping body of the otoscope and the ear speculum cover being attached onto the ear speculum of the otoscope, wherein the speculum cover has a fluid delivery passageway to form a fluid path from the fluid supply and dispensing container through the speculum cover for delivering fluid into the ear canal; and wherein the fluid delivery passageway of the speculum cover has an inlet connector end for attaching tubing to make a fluid tight seal between the speculum cover and the fluid supply and dispensing container.

2. The otoscope kit of claim 1 wherein the fluid dispensing means further comprises a pump, a tube connected to the fluid supply and dispensing container at one end extending and connected to a connector on the speculum cover.

3. An otoscope kit with an attachable ear wax removal device for ear wax removal comprising:

an otoscope having an elongated gripping body; a hollow conical ear speculum, having a small outer end adapted to be placed in the ear canal of a patient, said ear speculum being transversely connected to a top end of the gripping body; a viewing means connected to said top end of the gripping body to provide a line of sight through said ear speculum; a light source which is directed through the ear speculum;

a fluid dispensing means which is removably attached to the otoscope for ejecting fluid through a speculum cover into the ear canal, the fluid dispensing means having a fluid dispenser housing for holding a fluid supply container and dispenser, the fluid dispenser housing for holding a fluid supply and dispensing container, the fluid dispenser housing being mounted on the gripping body of the otoscope and the ear speculum cover being attached onto the ear speculum of the otoscope wherein the speculum cover has a fluid delivery passageway with a first inlet connector for attaching tubing to form a fluid path from the fluid supply and dispensing container through the speculum cover for delivering fluid into the ear canal; and wherein the fluid dispensing means further comprises a fluid recovery means having a vacuum pump, a fluid and debris recovery container and a tube for connecting the fluid recovery container to a second vacuum connector on the speculum cover.

4. The otoscope kit of claim 3 wherein the fluid dispensing means is controlled by an actuator switch that is mounted in an opening of said gripping body.

5. The otoscope kit of claim 3 wherein the speculum cover is removably attached over the smaller outer end of the ear speculum.

6. The otoscope kit of claim 3 wherein the fluid recovery means is controlled by a second actuator switch mounted in an opening of the gripping body.

7. The otoscope kit of claim 3 wherein the speculum cover further comprises a second vacuum fluid passageway extending through the speculum cover from the second connector to the small outer end to form a fluid and debris recovery passageway for recovering fluid and debris from the ear canal back into the fluid recovery container.

8. The otoscope kit of claim 7 wherein the fluid delivery connector is positioned on an external surface of the speculum cover.

9. The otoscope kit of claim 8 wherein the fluid and debris recovery second connector is positioned on an external surface of the speculum cover.

10. The otoscope kit of claim 7 wherein the actuation of the fluid dispensing means occurs without blocking the line of sight through the viewing means.

11. The otoscope kit of claim 3 further comprises a pair of power sources, one power source for operating the otoscope and one power source for the removable fluid dispensing means.

12. The otoscope kit of claim 11 wherein the power source for operating the otoscope is an electrical cord connected to the gripping body for connecting a plug into an electrical outlet for supplying power to the otoscope.

13. The otoscope kit of claim 3 wherein the speculum cover is disposable for replacement after each use.

14. The otoscope kit of claim 3 wherein the fluid supply and dispensing container is disposable to be replaced after use.

15. The otoscope kit of claim 3 wherein the fluid recovery container is disposable.

16. An otoscope kit with an attachable ear wax removal device for ear wax removal comprising:

an otoscope having an elongated gripping body; a hollow conical ear speculum, having a small outer end adapted to be placed in the ear canal of a patient, said ear speculum being transversely connected to a top end of the gripping body; a viewing means connected to said top end of the gripping body to provide a line of sight through said ear speculum; a light source which is directed through the ear speculum;

a fluid dispensing means which is removably attached to the otoscope for ejecting fluid through a speculum cover into the ear canal, the fluid dispensing means having a fluid dispenser housing being mounted on the gripping body of the otoscope and the ear speculum cover being attached onto the ear speculum of the otoscope;

a pair of power sources, one power source for operating the otoscope and one power source for the removable fluid dispensing means; and wherein the power sources are one or more batteries stored in the gripping body and one or more batteries stored in the fluid dispensing means.

17. The otoscope kit of claim 16 wherein the otoscope includes a recharging base for inserting the end of the otoscope for recharging the batteries.

* * * * *